United States Patent [19]  
Mortensen

[11] Patent Number: 4,498,480  
[45] Date of Patent: Feb. 12, 1985

[54] ADJUSTABLE PROBE BELT ASSEMBLY

[76] Inventor: John L. Mortensen, 270 Elm St., Windsor Locks, Conn. 06096

[21] Appl. No.: 510,261

[22] Filed: Jul. 1, 1983

[51] Int. Cl.³ .............................................. A61B 5/04
[52] U.S. Cl. ................................................. 128/644
[58] Field of Search .............................. 128/639–641, 128/644, 783, 790–793, 798, 802, 803

[56] References Cited  
U.S. PATENT DOCUMENTS

| | | | |
|---|---|---|---|
| 3,542,010 | 11/1970 | Love | 128/644 |
| 3,888,240 | 6/1975 | Reinhold, Jr. et al. | 128/644 |
| 4,026,278 | 5/1977 | Ricketts et al. | 128/644 |
| 4,121,575 | 10/1978 | Mills et al. | 128/644 |
| 4,202,344 | 5/1980 | Mills et al. | 128/644 |

Primary Examiner—Kyle L. Howell  
Assistant Examiner—Ruth Smith  
Attorney, Agent, or Firm—Donald S. Holland

[57] ABSTRACT

An adjustable probe belt assembly is disclosed for quickly hooking up different size patients to an electrocardiograph. The assembly has a weighted strip of material or "probe belt" that fits against a patient's chest, wherein the belt carries a set of eccentrically mounted electrodes that can be rotated so that their patient-contacting surfaces can be adjusted to fit the chest size of the particular patient.

The probe belt is preferably made of a disposable or washable material and the electrodes are especially designed so that they can be easily popped out or removed for disposability or cleaning of the belt. The electrodes can then be cleaned and snapped back into a fresh belt, which insures that the entire assembly will be sterile for the next patient's use.

16 Claims, 4 Drawing Figures

U.S. Patent     Feb. 12, 1985     4,498,480
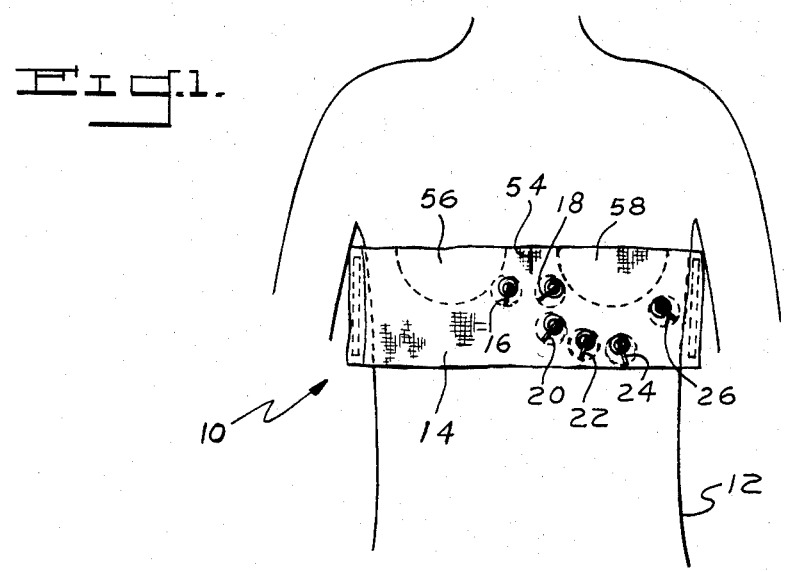
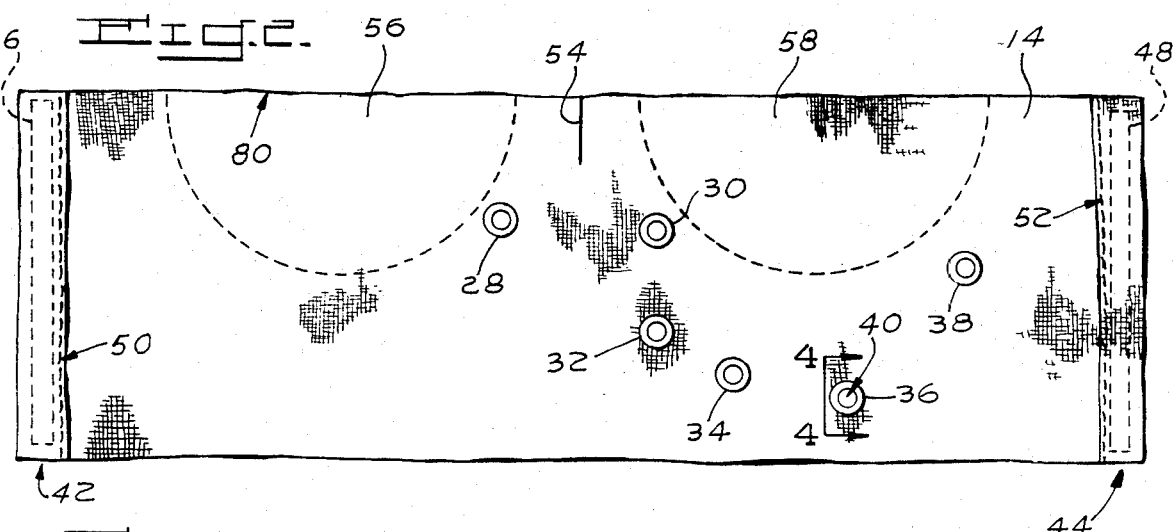
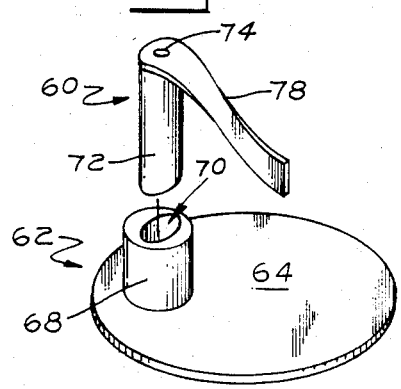
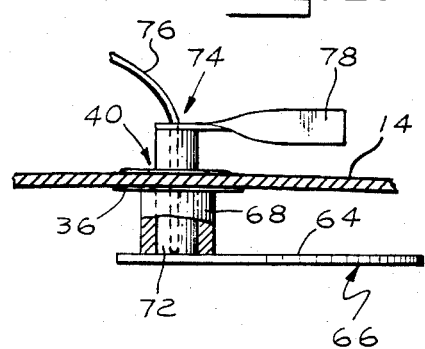

ADJUSTABLE PROBE BELT ASSEMBLY

BACKGROUND OF THE INVENTION

This invention relates to electrocardiographs and, more particularly, to "probe belts" that are used to hook up patients to the lead electrodes for electrocardiographs.

An electrocardiograph is an instrument used to record the electric impulses generated by the heart with each of its contractions or heartbeats. The impulses can be recorded on paper as a permanent graph, which is called an electrocardiogram ("ECG" or, more popularly, "EKG"). Or, they can be displayed for examination on an oscilloscope.

An EKG is a basic diagnostic indicator that tells the doctor about the condition of his patient's heart. The heart's wave patterns reveal any damage it may have suffered as a result of a coronary attack and how it is reacting to medicines, such as digitalis. The patterns also indicate certain abnormalities that may require further investigation or treatment.

During the early use of electrocardiographs, a single electrode was hooked up to a patient's chest, over his heart, and a comparator electrode (whose electric potential was close to the mean potential of the patient's body during the entire cardiac cycle was usually hooked up to the patient's leg or back. Recently, electrographs have been used with multiple electrodes to provide sufficient information to computers to have them produce three-dimensional models that show the spread of electrical impulses over the heart. By viewing the model, doctors can determine any "dead spots" or areas that are blocked.

Often, electrocardiographs are used in emergency rooms to quickly assess the damage that a heart attack victim has suffered. To be effective, the EKG must be quickly taken. The electrodes used to obtain the necessary information must be quickly attached to the patient's body and must be properly located.

Though the usual procedure is to apply the electrodes separately to the victim's chest with suction cups, this practice is laborious and requires the attention of a skilled nurse, technician or doctor. Further, the cups often come off during movement by the patient.

Accordingly, probe belts have recently been designed to rapidly apply a series of electrocardiograph electrodes to a patient's body by placing a belt onto the wearer's chest that carries a series of these electrodes. By placing the belt onto the wearer's chest, the electrodes are applied simultaneously.

While these belts have generally proved useful, they have had their drawbacks. Some cannot be adjusted so that their electrodes fit the various chest sizes or configurations of different users. Others, such as those shown in U.S. Pat. Nos. 4,121,575 and 4,202,344 to Mills et al, can be adjusted to a limited extent, but only after they have been wrapped around the patient's upper torso and fastened behind his back.

Another drawback is that these belt assemblies are generally expensive and not disposable. Further, they are often difficult to clean. As a result, the assemblies are generally kept after prior uses and are not always sterile for future use.

Sometimes the assemblies are used for assessing the heart condition of bloodied accident victims. Obviously, in those kind of instances, it would make sense if the assembly were easily disposable or could be easily cleaned.

Accordingly, it is a primary object of the present invention to provide an improved probe belt assembly that overcomes the above-described deficiencies of the prior art.

It is therefore a general object of the invention to provide an improved probe belt assembly that can be quickly adjusted to fit the chest size of most patients.

It is a more specific object to provide a probe belt that can be quickly hooked up to a patient without fastening the belt behind the wearer's back, wherein the belt includes a weighted strip that fits against the wearer's chest and the belt carries a series of eccentrically mounted electrodes that can be rotated so that their patient-contacting surfaces can be quickly adjusted to fit the patient's particular chest size.

It is another general object to provide an improved probe belt assembly with components that are easily disposable or cleanable.

It is a more specific object to provide a probe belt assembly with a belt that is made of disposable or easily cleanable material, wherein the electrodes that the belt carries are specially designed so that they can be easily popped out or removed for disposability or cleaning of the belt.

It is a further object to provide an improved probe belt assembly that is economical and simple in design, yet durable and highly effective to use.

The above and other objects and advantages of this invention will become more readily apparent when the following description is read in conjunction with the accompanying drawings.

BRIEF DESCRIPTION OF THE DRAWINGS

FIG. 1 is a schematic view of an adjustable probe belt assembly that is constructed in accordance with the present invention and hooked up to a representative patient;

FIG. 2 is a top plan view of the assembly's belt laid flat, with its electrodes removed;

FIG. 3 is an exploded view of one of the electrodes; and,

FIG. 4 is a cross-sectional view of a portion of the assembly shown in FIG. 1, taken along 4—4 of FIG. 2, showing a close-up view of an electrode attached to the belt.

DETAILED DESCRIPTION OF THE PREFERRED EMBODIMENTS

Referring to the drawings in detail, an adjustable probe belt assembly 10 is illustrated for quickly hooking up a patient (such as the representative one shown at 12) to an electrocardiograph (not shown). The assembly includes a weighted probe belt 14 that can be draped across the chest of a prone patient, wherein the belt carries a set of eccentrically mounted, metal electrodes or probes 16, 18, 20, 22, 24, 26 that can be rotated so that the assembly can be adjusted to fit the chest size of the particular patient.

As best shown in FIGS. 1 and 2, the belt 14 is preferably made of a disposable sheet of material, such as paper, and includes a series of grommets 28, 30, 32, 34, 36, 38 for carrying the electrodes. When the belt is made of paper, the grommets can also be made of paper (though heavier) and they serve to prevent the belt from being ripped by the heavier electrodes. They have round holes 40 and permit the electrodes to be freely rotated to their proper positions for recording data.

The belt 14 has pockets 42, 44 at its ends for slidably housing removable weights 46, 48. These pockets are each formed by doubling over the ends and securing them to the remainder of the belt by any suitable means, such as glue along lines 50, 52. Due to the weights, the belt can be quickly slipped onto the patient's chest and held in position by dropping the weighted ends over the patient's sides.

Alternatively, the weights 46, 48 can be clip-on units (not shown) that can be easily attached and subsequently removed from the belt 14. For example, the weights can each have a spring-loaded clip that can be squeezed open like a clipboard to attach the weights to the ends of the belt.

To properly align the belt on a patient, the belt includes a center line 54 that can be mated up with the center of the patient's sternum. Further, the belt includes a pair of perforated breast cut-outs 56, 58 that can be easily removed so that the belt can be properly under a female patient's breasts.

FIG. 3 shows one of the identical electrodes used in the preferred embodiment. Each electrode is specially designed so that it can be quickly adjusted in the belt 14 to fit the contours of the particular patient. Further, they are also designed so that they can be easily popped out or removed from the grommets for easy disposability of the belt.

To achieve this, the electrodes comprise upper and lower "snap-together" halves 60, 62 that are positioned on opposite sides of the belt, with the upper half 60 being positioned above the belt when it is "attached" to a patient and the lower half 62 being positioned below the belt, as shown in phantom in FIG. 1. The lower half 62 comprises an electrically conductive, round metal disk 64 with an underlying surface 66 that contacts the patient's chest when the assembly is being properly used. The disk 64 has an integral, eccentric mounting post 68 that extends perpendicularly and which includes an oval channel 70 for removably receiving a complementary shaped, hollow stem 72 of the electrode's upper half 60.

In addition to the stem, the upper half 60 includes a hole 74 for removably receiving a lead wire 76 from the electrocardiograph. In the assembled position shown in FIG. 4, the wire 76 fits through the hole 74 and into the channel 70, where it preferably rests against the top of the disk. To insure proper conductivity, the stem and channel can be filled with the same type of electrolytic paste or gel that is traditionally used on the bottom of electrodes for normally providing a low-resistant contact between the electrode and the patient's skin.

For the sake of simplicity, the lead wires 76 have been eliminated from FIG. 1. It should, however, be understood that each of the electrodes has such a wire, as shown in FIG. 4.

To assemble each of the electrodes, the lower half 62 is placed under the belt 14, with its mounting post 68 aligned with the round hole 40 of the particular grommet. The stem 72 is then placed through the hole 40 into the other side, where it is press fit into the channel 70.

As best shown in FIG. 4, the diameter of mounting post 68 is larger than the hole 40 in the grommet while the oval stem 70 is smaller. This insures that the post will not slip up through the grommet, but instead be pressed against the patient's chest. Further, the smaller stem permits the disk to be easily rotated by manually turning an arm 78 that is fixed to the stem. This arm preferably has a 90° twist to make it easier to grasp.

Though not shown, the stem 72 can include an integral ring or washer near arm 78 to insure that the upper half 62 will not slip down through the grommet when the belt is lifted or moved. This ring would be located in the stem portion shown above grommet 36 in FIG. 4.

Since the channel 70 and stem 72 are complementary shaped and not round, rotation of the arm 78 causes the underlying disk 64 to turn with it. Further, since the post 68 is eccentrically mounted, when the arm 78 is rotated, the disk (shown in phantom in FIG. 1) turns through a much larger arc than it would if the post were centrally located.

Because the disk can be rotated over a larger area, the disk's patient-contacting surface 66 can be repositioned to fit the chest size of the particular patient. In other words, the disk can be rotated until it is in its proper anatomical position for sending the required data to the electrocardiograph.

To use the assembly 10, the belt 14 is first slipped onto the user's chest. The center line 54 is aligned with the patient's sternum and the rotator arms 78 are turned to quickly adjust the electrodes to fit the patient's chest. The weights 46, 48 hold the electrodes in their proper positions for sending data to the electrocardiograph.

Once the assembly 10 is used, the electrodes are popped out for disposability of the belt 14. The electrodes are then cleaned and snapped back into a fresh belt, which insures that the entire assembly will be sterile for the next patient's use.

Though the belt 14 has been disclosed as being made of paper, for inexpensive disposability after use, it can also be made of a washable material, such as cotton or terry cloth. When the material is washable, the pockets 42, 44 can be formed by stitching the doubled-over end portions along lines 50, 52 or by using VELCRO ® fastener strips. Further, when the material is washable cloth, the breast cut-outs 56, 58 can be deleted in favor of a straight-cut top line 80 of fabric.

It should be understood by those skilled in the art that obvious structural modifications can be made without departing from the spirit or scope of the invention. For example, while the channel 70 and stem 72 have been disclosed as oval, they can be any shape that permits the stem 72 and post 68 to rotate together. Accordingly, reference should be made primarily to the appended claims, rather than to the foregoing specification, to determine the scope of the invention.

Having thus described the invention, what is claimed is:

1. An adjustable probe belt assembly for hooking up a patient to an electrocardiograph, said assembly comprising:
   (a) a sheet of material having a pocket at each end with a weight inside, wherein said sheet is adapted in length to fit across the chest of a patient with the weights draped over the patient's sides and said sheet has a plurality of spaced grommets for housing detachable electrodes;
   (b) a plurality of electrodes respectively mounted within said grommets for eccentric rotation therein: and,
   (c) wherein each electrode includes a lower portion on one side of said sheet for contacting the patient's skin and an upper portion on the other side of the sheet for adjusting the location of the patient-contacting portion on the patient's chest, said electrode's lower portion comprising a metal disk with an undersurface for contacting the patient and an eccentrically mounted post that extends perpendicularly from the top surface of the disk toward the grommet in which the electrode is mounted, said post having a channel for removably receiving a stem of said upper electrode portion, said upper portion having a rotator arm on the opposite side of said sheet from said disk, wherein said arm is integral with a stem that fits through a hole in said grommet and into the channel of said post, whereby said electrodes can each be eccentrically rotated through a wide arc by turning their arms to quickly adjust the disks to fit the particular patient's chest size.

2. The probe belt of claim 1 wherein the post's channel is oval and the stem is complementary shaped so that the stem and post turn together as the rotator arm is turned, and they can be quickly detached from one another.

3. The probe belt assembly of claim 1 wherein the sheet is made of paper and includes a pair of perforated breast cut-outs that can be removed so that the sheet can be slipped under a female patient's breasts.

4. The probe belt assembly of claim 1 wherein the stem is hollow and includes a hole at one end for slidably receiving a lead wire from the electrocardiograph.

5. The probe belt assembly of claim 2 wherein the sheet is made of cotton and the grommets are made of metal.

6. The probe belt assembly of claim 2 wherein the rotator arm has a free end that extends from the stem and which is twisted to provide a grip for a user's fingers.

7. An adjustable probe belt assembly for hooking up a patient to an electrocardiograph, said assembly comprising:
(a) a sheet of material having a pocket at each end with a weight inside, wherein said sheet is adapted in length to fit across the chest of a patient with the weights draped over the patient's sides and said sheet has a plurality of spaced grommets for housing detachable electrodes;
(b) a plurality of electrodes rotatably mounted within said grommets; and,
(c) means for quickly adjusting the electrodes so that their patient-contacting surfaces can be relocated to fit the size of the particular patient's chest so that the electrodes are properly anatomically located for sending proper electrical signals from the patient's heart to the electrocardiograph, said adjusting means comprising said electrodes each having a patient-contacting disk on one side of the sheet with an eccentrically mounted post being integral with the disk and extending perpendicularly therefrom toward the grommet in which it is mounted, said electrode having a rotator portion on the other side of said sheet, said rotator portion having a stem detachably extending through the grommet and into a channel in said post, said rotator portion having an arm extending from said stem whereby said disk can be eccentrically rotated through a wide arc to properly locate the electrode anatomically on the patient's chest after the sheet is placed on the patient.

8. The probe belt of claim 7 wherein the post's channel is oval and the stem is complementary shaped so that the stem and post turn together as the rotator arm is turned, and they can be quickly detached from one another.

9. The probe belt assembly of claim 7 wherein the sheet is made of paper and includes a pair of perforated breast cut-outs that can be removed so that the sheet can be slipped under a female patient's breasts.

10. The probe belt assembly of claim 7 wherein the stem is hollow and includes a hole at one end for slidably receiving a lead wire from the electrocardiograph.

11. The probe belt assembly of claim 8 wherein the sheet is made of cotton and the grommets are made of metal.

12. The probe belt assembly of claim 8 wherein the rotator arm has a free end that extends from the stem and which is twisted to provide a grip for a user's fingers.

13. An adjustable probe belt assembly for hooking up a patient to an electrocardiograph, said assembly comprising:
(a) a probe belt that is adapted in size and shape to be draped across the patient's chest, wherein said belt has a plurality of spaced grommets for housing detachable electrodes;
(b) a plurality of electrodes respectively and rotatably mounted in said grommets; and,
(c) means for quickly relocating the positions of the electrodes to fit the patient's chest after the belt is draped over the patient, said means comprising said electrodes each having a patient-contacting disk on one side of said belt, wherein said disk has an eccentric post extending perpendicularly therefrom toward the grommet in which the electrode is mounted and wherein the disk is connected to an upper rotator portion on the other side of the belt by a stem that fits through the grommet and into a complementary shaped channel in the post, whereby said electrodes can be eccentrically rotated through a wide arc to be placed at the proper anatomical positions on the particular patient's chest for properly sending data to the electrocardiograph.

14. The probe belt assembly of claim 13 wherein the diameter of the post is greater than the diameter of a hole in the grommet so that the disk does not slip through the grommet and is pushed against the patient's chest when the belt is draped over the patient.

15. An adjustable probe belt assembly for hooking up a patient to an electrocardiograph, said assembly comprising:
(a) a paper sheet having a pocket at each end with a slidably removable weight housed inside, wherein said sheet is adapted in length to fit across the chest of a patient with the weights draped over the patient's sides, said sheet has a plurality of spaced grommets for housing detachable electrodes, and said sheet has a pair of perforated breast cut-outs that can be removed so that the sheet can be slipped under a female patient's breasts:
(b) a plurality of electrodes respectively mounted within said grommets for eccentric rotation therein; and
(c) wherein each electrode includes a lower portion on one side of said sheet for contacting the patient's skin and an upper portion on the other side of the sheet for adjusting the location of the patient-contacting portion on the patient's chest, said electrode's lower portion comprising a round metal disk with an undersurface for contacting the patient and an eccentrically mounted post that is integral with the disk and extends perpendicularly from the top of it toward the grommet in which the electrode is mounted, said post having a channel for removably receiving a stem of said upper electrode portion, said upper portion having a rotator arm on the opposite side of said sheet from said disk, wherein said arm is integral with a stem that fits through a hole in said grommet and into the channel of said post and said arm has a free end that extends from the stem and which is twisted to provide a grip for a user's fingers, and wherein said stem is hollow and includes a hole at one end for slidably receiving a lead wire from the electrocardiograph, whereby said electrodes can each be eccentrically rotated through a wide arc by turning their arms to properly locate the electrodes anatomically on the patient's chest after the sheet is placed on the patient.

16. A method of hooking a patient up to an electrocardiograph:
    (a) draping a sheet of material over the patient's chest, wherein the sheet carries a plurality of eccentrically rotatable electrodes;
    (b) draping weighted ends of the sheet over the patient's sides to hold the sheet in place; and,
    (c) adjusting the electrodes to fit the size of the particular patient's chest by eccentrically rotating the electrodes until their patient-contacting surfaces are in the proper anatomical positions for sending the correct data from the patient's heart to the electrocardiograph.

* * * * *